US009057685B2

(12) United States Patent
Allen et al.

(10) Patent No.: US 9,057,685 B2
(45) Date of Patent: Jun. 16, 2015

(54) SAMPLE VISCOSITY AND FLOW CONTROL FOR HEAVY SAMPLES, AND X-RAY ANALYSIS APPLICATIONS THEREOF

(75) Inventors: George Allen, Middle Grove, NY (US); Stuart Shakshober, Hudson, NY (US); Sony Cheriyan, Jersey City, NJ (US)

(73) Assignee: X-RAY OPTICAL SYSTEMS, INC., East Greenbush, NY (US)

( * ) Notice: Subject to any disclaimer, the term of this patent is extended or adjusted under 35 U.S.C. 154(b) by 243 days.

(21) Appl. No.: 13/584,978

(22) Filed: Aug. 14, 2012

(65) Prior Publication Data

US 2013/0044858 A1    Feb. 21, 2013

Related U.S. Application Data

(60) Provisional application No. 61/523,605, filed on Aug. 15, 2011.

(51) Int. Cl.
*G01N 23/223* (2006.01)
*G01N 33/28* (2006.01)
*H01J 35/16* (2006.01)

(52) U.S. Cl.
CPC .......... *G01N 23/223* (2013.01); *G01N 33/2823* (2013.01); *H01J 35/16* (2013.01); *H01J 2235/18* (2013.01); *G01N 2223/076* (2013.01)

(58) Field of Classification Search
CPC . G01N 23/223; G01N 2223/076; G21K 1/06; A61B 6/485
USPC ........................................ 378/44, 45, 47, 208
See application file for complete search history.

(56) References Cited

U.S. PATENT DOCUMENTS

| 5,712,891 | A | 1/1998 | Benony et al. |
| 7,016,462 | B1 | 3/2006 | Keville et al. |
| 7,697,141 | B2 | 4/2010 | Jones et al. |
| 2006/0093086 | A1* | 5/2006 | Gallagher ........................ 378/45 |
| 2009/0213988 | A1 | 8/2009 | Chen et al. |

OTHER PUBLICATIONS

Allen et al., Notification of Transmittal of the International Search Report and the Written Opinion of the International Searching Authority, or the Declaration, for PCT/US2012/050708, dated Feb. 26, 2013.

* cited by examiner

*Primary Examiner* — Courtney Thomas
(74) *Attorney, Agent, or Firm* — Jeff Klembczyk, Esq.; Kevin P. Radigan, Esq.; Heslin Rothenberg Farley & Mesiti P.C.

(57) ABSTRACT

An x-ray analysis system having an x-ray engine with an x-ray source for producing an x-ray excitation beam directed toward an x-ray analysis focal area; a sample chamber for presenting a sample stream to the x-ray analysis focal area, the analysis focal area disposed within a sample analysis area defined within the chamber; an x-ray detection path for collecting secondary x-rays and directing the x-rays toward a detector; an x-ray transparent barrier on a wall of the chamber through which the x-rays pass; and a blocking structure partially blocking the sample analysis area, for creating sample stream turbulence in the sample analysis area and over the barrier. The blocking structure may be disposed asymmetrically about a central axis of the x-ray analysis focal area and/or the sample analysis area; and may be a rounded pin. A heating element may be used to heat the sample stream for improving flow.

20 Claims, 7 Drawing Sheets

SAMPLE VISCOSITY AND FLOW CONTROL FOR HEAVY SAMPLES, AND X-RAY ANALYSIS APPLICATIONS THEREOF

CROSS-REFERENCE TO RELATED PATENT APPLICATION

This application claims the benefit of U.S. provisional patent application Ser. No. 61/523,605, filed Aug. 15, 2011, which is hereby incorporated herein by reference in its entirety.

TECHNICAL FIELD

This invention relates in general to apparatus and methods used for x-ray analysis of sample streams. More particularly, the present invention is directed to viscosity and flow control techniques for presenting a heavy sample stream to an x-ray analysis focal area in an x-ray analysis system.

BACKGROUND OF THE INVENTION

X-ray analysis of samples is a growing area of interest across many industries such as medical, pharmaceutical, and petroleum. The use of x-ray fluorescence, x-ray diffraction, x-ray spectroscopy, x-ray imaging, and other x-ray analysis techniques has led to a profound increase in knowledge in virtually all scientific fields.

X-ray fluorescence (XRF) is an analytical technique by which a substance is exposed to a beam of x-rays to determine, for example, the presence of certain components. In XRF, at least some of the elemental constituents of the substance exposed to x-rays can absorb x-ray photons and produce characteristic secondary fluorescence. These secondary x-rays are characteristic of the elemental constituents in the substance. Upon appropriate detection and analysis these secondary x-rays can be used to characterize one or more of the elemental constituents. XRF techniques have broad applications in many chemical and material science fields, including industrial, medical, semiconductor chip evaluation, petroleum, and forensics, among others.

As some examples of measurements required in the petroleum industry, trace levels of contaminants in petroleum feedstocks is a notorious problem in petroleum refining. Sulfur is a common component in crude oil streams—and its removal from final product is mandated due to its impact on the environment, as regulated by the US EPA under the Clean Air Act. Sulfur is harmful to the environment, and the cost of its removal is high. Therefore, monitoring sulfur levels early in the refining process is important. Chlorine and vanadium contaminants are considered "bad actors" by the refining industry for primarily non-regulatory, process control reasons. Chlorides also pose one of the greatest problems to the refining industry. According to a 2005 paper by The National Association of Corrosion Engineers ("NACE"): "Recently, an increasing number of refineries have experienced extreme corrosion and fouling in crude distillation unit overheads and/or naphtha hydrotreating units. The root causes were traced to severe spikes in the chloride levels."

U.S. Pat. Nos. 6,934,359 and 7,072,439, hereby incorporated by reference herein in their entirety and assigned to X-Ray Optical Systems, Inc., the assignee of the present invention, disclose monochromatic wavelength dispersive x-ray fluorescence (MWD XRF) techniques and systems for the analysis of liquid samples. Moreover, commonly assigned U.S. Pat. No. 7,277,527 (also included by reference in its entirety) entitled "MOVABLE TRANSPARENT BARRIER FOR X-RAY ANALYSIS OF A PRESSURIZED SAMPLE" addresses a particular problem inherent in moving sample streams in such systems as discussed further below.

As one particular example of a measurement system for such contaminants, the above-incorporated patents disclose techniques for the determination of the level of elements in petroleum fuels, and a commercialized analyzer (SINDIE) is now in widespread use for, e.g., sulfur measurement at petroleum refining, pipeline, and terminal facilities.

XRF fluid testing can take place off-line, i.e., using a bench-top, laboratory-type instrument to analyze a sample. The material is removed from its source (e.g., for fuel, from a refinery or transportation pipeline) and then simply deposited in a sample chamber; or into a windowed sample cell which is then deposited into a chamber. Off-line, bench-top instruments need not meet any unusual operational/pressure/environmental/size/weight/space/safety constraints, but merely need to provide the requisite measurement precision for a manually-placed sample. Moreover, off-line instruments can be easily maintained between measurements.

In contrast to off-line analysis, on-line analysis provides "real-time" monitoring of sample composition at various points in the manufacturing process. For example, all fuel products are subject to sulfur level compliance—requiring some variant of on-line monitoring during fuel refining and transportation in pipelines. On-line analysis of fuels in a refinery and in pipelines, however, requires consideration of numerous operational issues not generally present in an off-line, laboratory setting. A fully automated fuel sample handling system is required—with little or no manual intervention or maintenance. Also, since fluids are usually under pressure in pipelines, any sample handling system must account for pressure differentials. This is especially important since certain portions of XRF x-ray "engines" (discussed further below) operate in a vacuum. Also, the instrument's electronics require packaging in an explosion-proof housing—separate from the sample handling system.

In an on-line analyzer for crude and heavy fuel applications, differing sample stream viscosities make it challenging to present samples to the analyzer at a stable pressure and flow rate. Chlorine measurement presents another challenge because the chlorine mostly exists in water phase, which may not mix homogeneously in crude.

In these applications one of the most critical components is the sample barrier(s) which allow photons of the x-rays to excite sulfur atoms in the fluid, and photons emitted from the atoms to be counted at the engine's detector, while at the same time maintaining the vacuum in the x-ray engine and the pressure of the fluid. X-ray stimulation may create sulfur (or other hard element) ionization and adsorption at this interface over time and on certain types of barrier materials—leading to undesired sulfur residue and degradation of the barrier's x-ray transparency. More generally, many XRF applications require a barrier to protect the engine from any number of adverse interface effects from the sample material and/or the measurement environment.

The barrier system of above-incorporated U.S. Pat. No. 7,277,527 offered a very important and successful solution to these problems in the form of a moveable barrier advanced at programmable intervals to clean portions of a window roll, however, it is still desirable to provide techniques which keep this interface clean, and the sample stream moving through the sample cell at a desirable rate and consistency.

What is required, therefore, are lower cost and lower maintenance sample handling techniques for an on-line x-ray analysis system handling high viscosity samples, which protects the x-ray engine from adverse sample and environmental effects, while maintaining the integrity and transparency of the interface to the sample for accurate measurements without excessive moving parts.

SUMMARY OF THE INVENTION

The shortcomings of the prior art are overcome and additional advantages are provided by the present invention which in one aspect is an x-ray analysis system having an x-ray engine with an x-ray source for producing an x-ray excitation beam, the x-ray excitation beam directed toward an x-ray analysis focal area; a sample chamber for presenting a sample stream to the x-ray analysis focal area, the x-ray analysis focal area disposed within a sample analysis area defined within the chamber; an x-ray detection path for collecting secondary x-rays from the focal area and directing the secondary x-rays toward a detector; an x-ray transparent barrier on a wall of the chamber through which the x-ray excitation beam and the secondary x-rays pass; and a blocking structure partially blocking the sample analysis area, for creating sample stream turbulence in the sample analysis area and over the barrier.

The blocking structure may be disposed asymmetrically about a central axis of the x-ray analysis focal area and/or the sample analysis area; and may be a rounded pin.

In one embodiment, a heating element may be used to heat the sample stream for improving flow of the sample stream.

The focal area may be a focal point, defined by focused x-rays to/from at least one focusing optic in the x-ray excitation path and/or the x-ray detection path. The focusing optic may be a curved diffracting optic or a polycapillary optic.

The system may comprise a monochromatic wavelength-enabled XRF analyzer; e.g., an MWDXRF or ME-EDXRF analyzer.

The sample may comprise a low or high viscosity petroleum- based product requiring the measurement of an analyte therein, e.g., one or more elements chosen from the following list: S, Cl, P, K, Ca, V, Mn, Fe, Co, Ni, Cu, Zn, Hg, As, Pb, and Se.

Further, additional features and advantages are realized by the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in combination with the accompanying drawings in which:

DETAILED DESCRIPTION OF THE INVENTION

Figure 1:
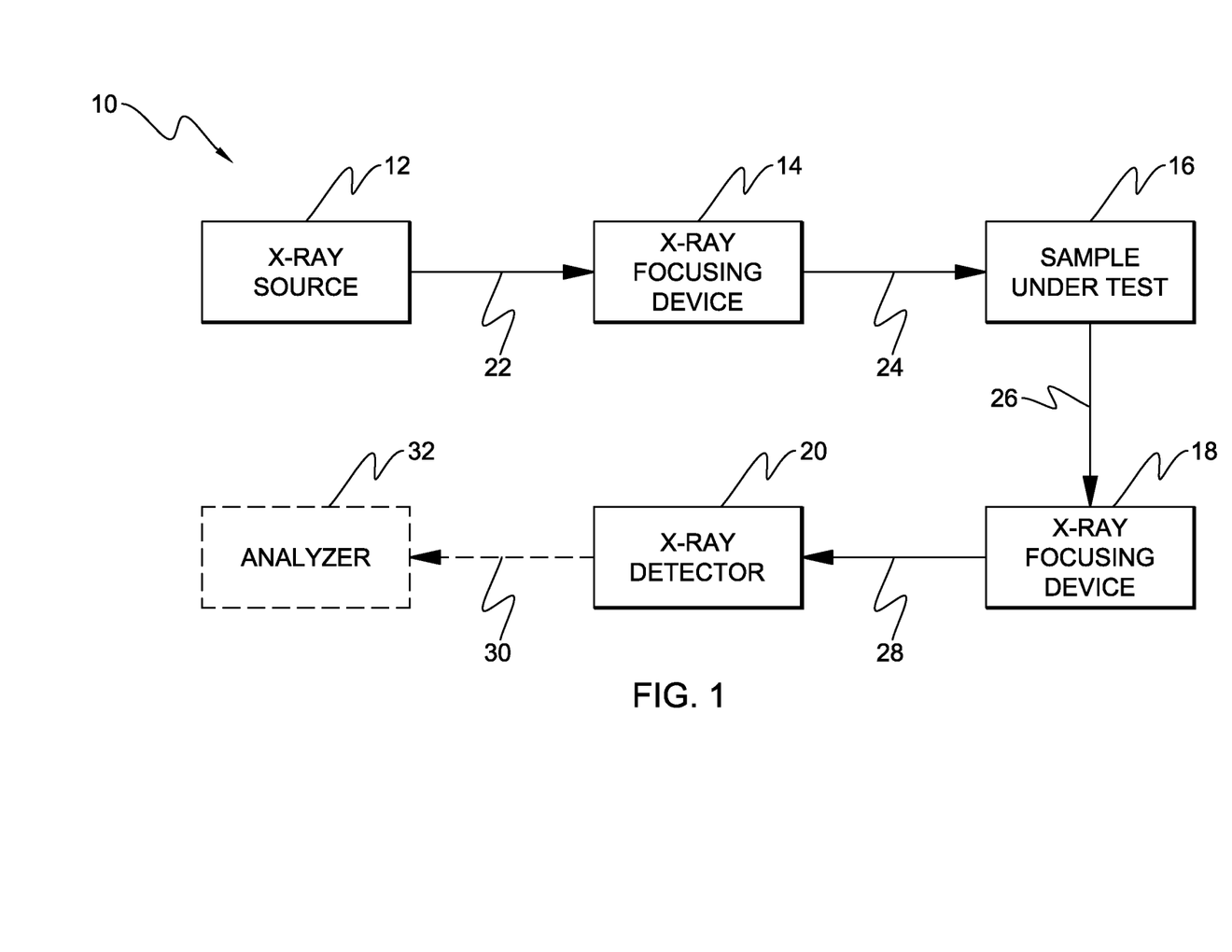
FIG. 1 is a functional block diagram of the elements of an exemplary x-ray fluorescence system.

FIG. 1 is a functional block diagram of a typical MWD XRF system 10 used for exposing a sample to x-ray radiation to produce fluorescent radiation which can then be detected and analyzed to determine a characteristic of the sample. The system may include an x-ray source 12, a first x-ray focusing device 14, a sample chamber 16, a second x-ray focusing device 18, and an x-ray detector 20. The x-ray source 12, for example, an x-ray tube, produces a beam of x-rays 22. Though x-rays are used throughout the specification, the invention extends to neutron, particle-beam or gamma ray radiation. Beam 22 may diffracted or focused by means of one or more x-ray focusing optics 14 as discussed further below.

The sample under test in sample chamber 16 may be any desired substance for which a characteristic measurement is desired. If the sample is static (in, for example, an off-line system), the sample is typically located on a relatively flat surface, for example, an x-ray reflective flat surface or an optically-reflective surface. The sample, if a solid, liquid, or gas, may also be contained in a closed container or chamber, for example, a sealed container, having an x-ray transparent aperture through which x-ray beam can pass. The present invention is directed to, in general, low or high viscosity samples in streamable form (e.g., particulate, powders, liquid, gas, or a liquid-based material (e.g. slurry with particulate matter)) required to be moved through a chamber, and which exert some other potentially disruptive forces or effects within the chamber.

When irradiated by beam 24, at least one of the constituents of sample in chamber 16 is excited in such a fashion that the constituent fluoresces, that is, produces a secondary source of x-rays 26 due to excitation by x-rays 24. Again, since x-ray beam 26 is typically a diverging beam of x-rays, beam 26 is focused by means of the second x-ray focusing device 18, for example, a device similar to device 14, to produce a focused beam of x-rays 28 directed toward x-ray detector 20.

X-ray detector 20 may be a proportional counter- type or a semiconductor type x-ray detector (e.g., silicon drift detector), or any other suitable type of x-ray fluorescence detector known to one skilled in the art. Typically, x-ray detector 20 produces an electrical signal 30 containing at least some characteristic of the detected x-rays which is forwarded to an analyzer 32 for analysis, printout, or other display.

Figure 2:
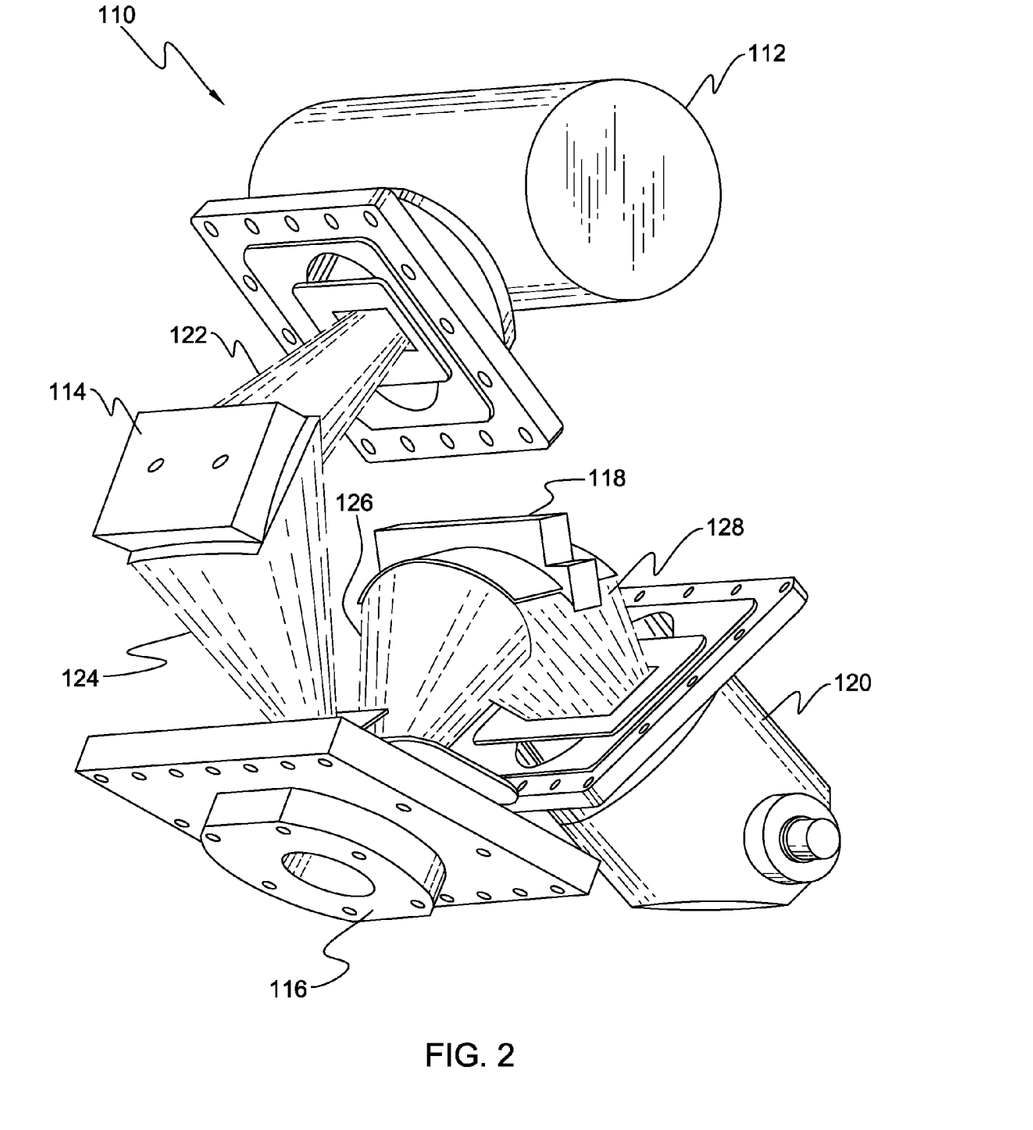
FIG. 2 is an isometric view of an exemplary x-ray fluorescence source/detection "engine" with an exemplary sample chamber.

FIG. 2 illustrates an MWD XRF x-ray engine assembly 110 according to the above-incorporated U.S. Pat. No. 7,072, 439 entitled "X-RAY TUBE AND METHOD AND APPARATUS FOR ANALYZING FLUID STREAMS USING X-RAYS." This is an example of a sulfur in fuels analysis system, and also employing the principles of monochromatic X-Ray excitation and collection as set forth in the above-incorporated U.S. Pat. No. 6,934,359 entitled "WAVELENGTH DISPERSIVE XRF SYSTEM USING FOCUSING OPTIC FOR EXCITATION AND A FOCUSING MONOCHROMATOR FOR COLLECTION." X-ray engine assembly 110 (shown with its housing removed) comprises an x-ray source assembly 112, a sample chamber interface 116 and an x-ray detector assembly 120. A curved crystal, monochromating and focusing optic 114 is shown in the excitation path, along with another curved crystal focusing optic 118 in the detection path. X-ray source assembly 112 produces an x-ray beam 122 which is focused by x-ray focusing optic 114 to produce a focused beam 124 on a sample under test in chamber assembly 116. The x-ray fluorescence created by the x-ray irradiation of the sample in sample excitation chamber assembly 116 generates x-ray fluorescent beam 126. Beam 126 is focused by x-ray focusing device 118 to provide a focused x-ray beam 128 which is directed to x-ray detector assembly 120.

The x-ray optics may include, for example, curved crystal monochromating optics such as those disclosed in commonly assigned U.S. Pat. Nos. 6,285,506; 6,317,483; 7,035,374; and 7,738,629; and/or multilayer optics; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506; 7,209,545; and 7,257,193 are also useable. Each of the above-noted patents is hereby incorporated herein by reference in its entirety.

Exemplary curved monochromating optics in the excitation and detection paths are shown in FIG. 2, which is the engine configuration of the SINDIE sulfur analyzer discussed above. However, an optic may only be present in one of these paths, which still requires precise alignment. In one example, an optic of any of the above-described types may only be present in the excitation path, and the detection path would include an energy dispersive detector. This is the configuration of a monochromatic excitation, energy dispersive x-ray fluorescence (ME-EDXRF) system. On-line, monochromatic excitation, energy dispersive x-ray fluorescence analyzers can also be used for these applications, in accordance with the present invention. The engine technology is disclosed in, e.g., commonly assigned PCT Publication No. WO 2009111454 (A1) entitled "XRF SYSTEM HAVING MULTIPLE EXCITATION ENERGY BANDS IN HIGHLY ALIGNED PACKAGE," the entirety of which is hereby incorporated by reference herein. In one embodiment this technique involves monochromatic excitation known as HD XRF. HD XRF is a multi-element analysis technique offering certain enhanced detection performance over traditional ED or WD XRF. This technique applies state-of-the-art monochromating and focusing optics, enabling multiple select-energy excitation beams that efficiently excite a broad range of target elements in the sample. Monochromatic excitation dramatically reduces scattering background under the fluorescence peaks, greatly enhancing elemental detection limits and precision. HDXRF is a direct measurement technique and does not require consumables or special sample preparation. Exemplary specifications for improved on-line analyzers using monochromatic-enabled x-ray excitation (including but not limited to ME-EDXRF and MWDXRF) include but are not limited to:

Exemplary elements measured: S, Cl, P, K, Ca, V, Mn, Fe, Co, Ni, Cu, Zn, Hg, As, Pb, and/or Se.

Sample T>cloud point, max 250 deg. F.

Viscosity 20 cSt or more

Filtration: 100 um

LOD: 0.3 ppm @300 s—aqueous matrix

LOD: 0.2 ppm @300 s—hydrocarbon matrix

Analysis Time: 10-900 s—user adjustable

Exemplary Range: 0.2 ppm/wt—3,000 ppm/wt (One of the key benefits of the disclosed on-line analyzer is its ability to measure both organic and inorganic chlorides.)

In certain methods of XRF detection, the sample excitation path and detection path are maintained in an inert gas atmosphere, for example, in a helium atmosphere. However, the unavailability of inert gases, especially in remote locations, makes the implementation of these prior art processes inconvenient. In contrast, here the sample excitation path and the detection path may be maintained under vacuum and no inert gas is necessary. For example, the radiation paths of system 110 shown in FIG. 2 may be held under vacuum, for example, at least about 15 torr. The vacuum can be provided by a venturi pump having no moving parts. However, if desired and available, an inert gas such as nitrogen or helium can be introduced and maintained in a housing, for example, under pressure.

The use of a vacuum enclosing the x-ray engine (e.g., source, excitation path, collection path, and detector) leads to certain problems at the sample interface—at the respective focal spots of beams 124 and 126. In FIG. 2, the engine's interface to the sample chamber 116 (discussed further below) may consist of a beryllium or kapton window barrier—which is strong and has the requisite x-ray transparency. But, additional levels of transparency are required when the sample chamber and its operational environment present certain operational difficulties as discussed above, especially in on-line systems.

Figure 3:
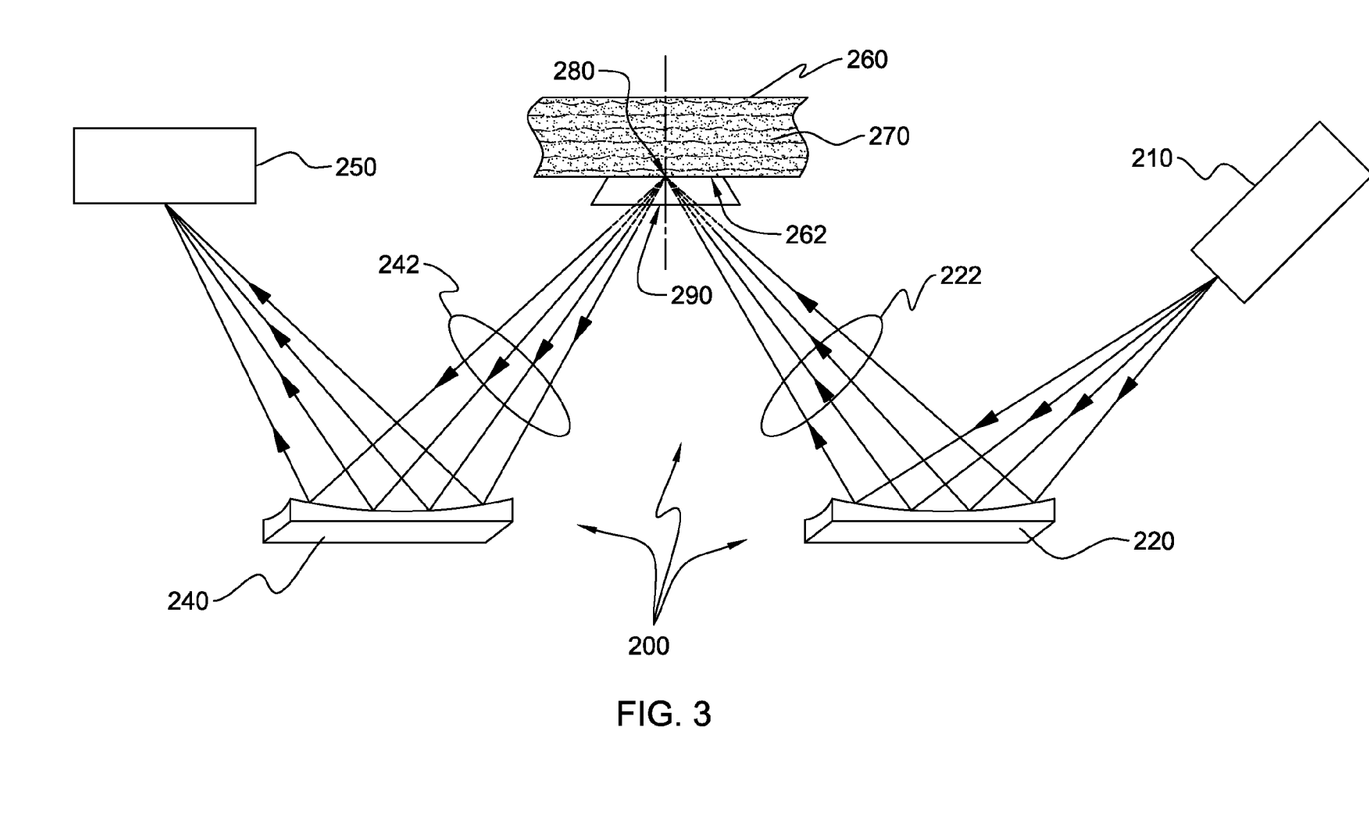
FIG. 3 is a schematic view of an MWD XRF analysis engine in combination with a sample chamber having a moving sample stream.

FIG. 3 depicts in schematic view an exemplary MWD XRF x-ray analysis engine 200, in combination with a sample chamber 260 carying a sample stream 270. As discussed above, the x-ray analysis engine may involve a focal area (created by excitation and/or detection optics) requiring alignment with the sample in the sample chamber. As discussed above. engine 200 includes, in one embodiment, an x-ray source 210 and detector 250. X-ray optics 220 and/or 240 can be placed in the excitation and/or detection paths of the engine. These optics require a high degree of alignment with the sample focal area to function at the requisite limits of detection discussed above.

Optic 220 focuses and monochromates the excitation x-rays 222 from the source 210 to a focal area 280 within the sample chamber 260. Optic 240 may also be used to focus the secondary fluorescence x-rays 242 from the focal area 280 to the detector 250. The excitation x-rays 222 and fluorescence x-rays 242 pass through an engine window barrier 290 (e.g., beryllium) and chamber barrier 262 to the focal area 280 within the chamber 260 and through which sample stream 270 flows. "Focal area" is used broadly herein to connote a sample analysis area to/from which x-rays are directed. In one embodiment, the focal area could be a small focal point with a diameter between 1-2 mm (or smaller) formed by converging excitation and/or fluorescence x-rays.

In this figure, the sample is presented into the sample chamber as a sample stream 270. The sample stream flows over the chamber's barrier 262 in this embodiment. The sample chamber could be part of a larger flow pipe system, a section of which is depicted in FIG. 3, and/or could be a relatively confined space (as discussed further below) with a sample inlet and outlet. Therefore, the term "sample chamber" is used broadly herein to connote any type of apparatus within which a sample stream can be defined, near the x-ray engine. The word "through" is broadly used herein to connote the stream passing directly through the focal area, or proximate thereto, with proximity being adequate enough to create the stimulation and/or fluorescent x-rays as required in a workable x-ray system.

Figure 4:
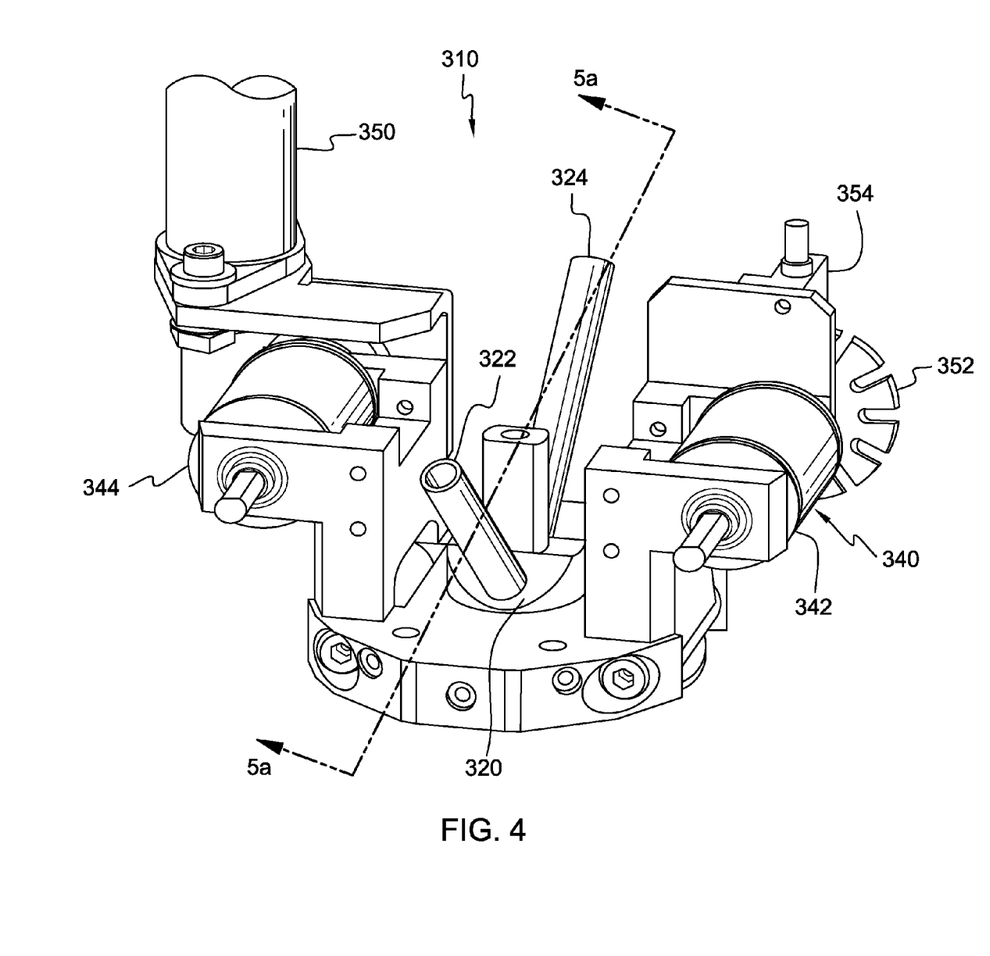
FIG. 4 is an isometric, solid view of a dynamic window module.

As discussed above, adsorption and other effects at the sample chamber barrier may impede proper measurement at this interface. With reference to FIG. 4, an improved sample handling apparatus, or "dynamic window module" 310 is depicted which is particularly suited to handle certain adverse conditions characteristic of on-line systems, in accordance with above-incorporated U.S. Pat. No. 7,277,527. The apparatus includes a sample chamber 320 having input 322 and output 324 sample ports for, e.g., particulate, liquid or gas moving through the system under pressure and requiring measurement. The apparatus includes a moveable barrier film 340 wound around a feed reel 342 and a take-up reel 344. The film, as discussed further below, runs past a sample aperture in a cavity at the bottom face of the chamber 320 (in fluid communication with the input and output ports) and provides an x-ray transparent barrier between the sample chamber and the x-ray engine discussed elsewhere herein. The barrier maintains compatibility with the environment from which the sample is drawn (e.g., pressurized) while maintaining the integrity of the x-ray engine, possibly itself under a vacuum.

In the embodiment shown, the take-up reel can be driven by a remotely-controlled motor 350 to move the film past a sample aperture at the bottom face of the chamber. A trigger wheel 352 and photo-electric sensor 354 can be used to remotely sense and report the amount of movement—using standard connections to a computer network (not shown). In this exemplary embodiment, the barrier movement may not be a continuous movement during sample measurement, rather, may either partially or fully "refresh" or "replace" areas of the barrier worn-out by adverse conditions, while maintaining the operating environments of both the x-ray engine and the sample handling apparatus.

Figure 5A:
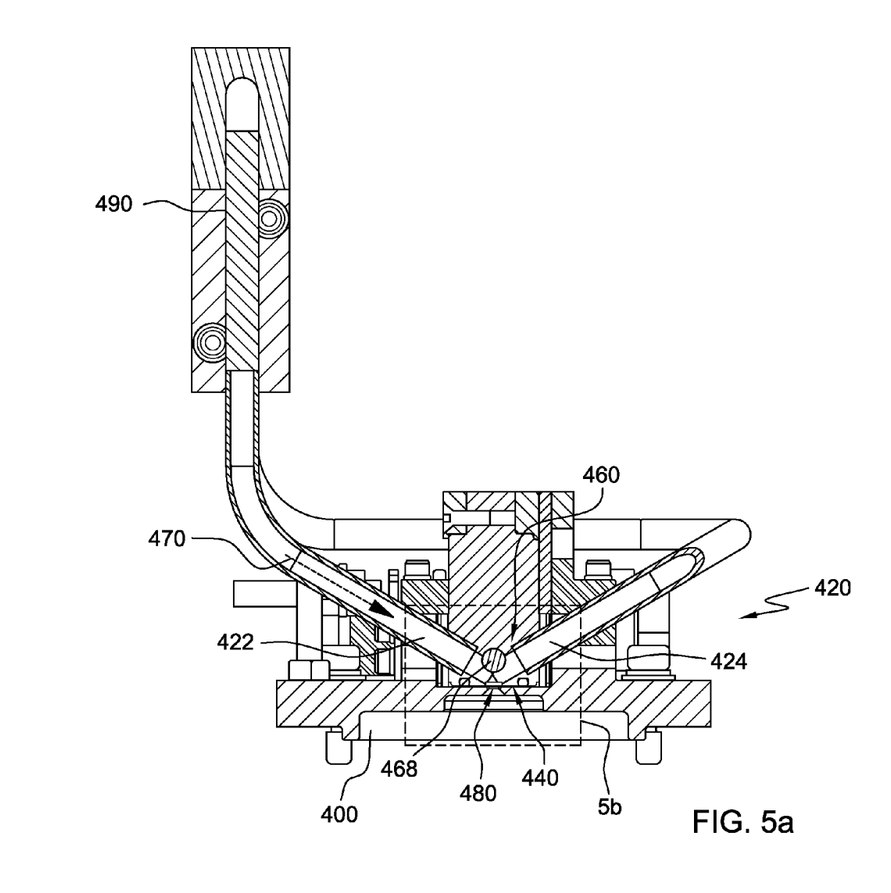
FIGS. 5a-b are partial cross-sectional views of an improved sample chamber in accordance with the present invention.
Figure 5B:
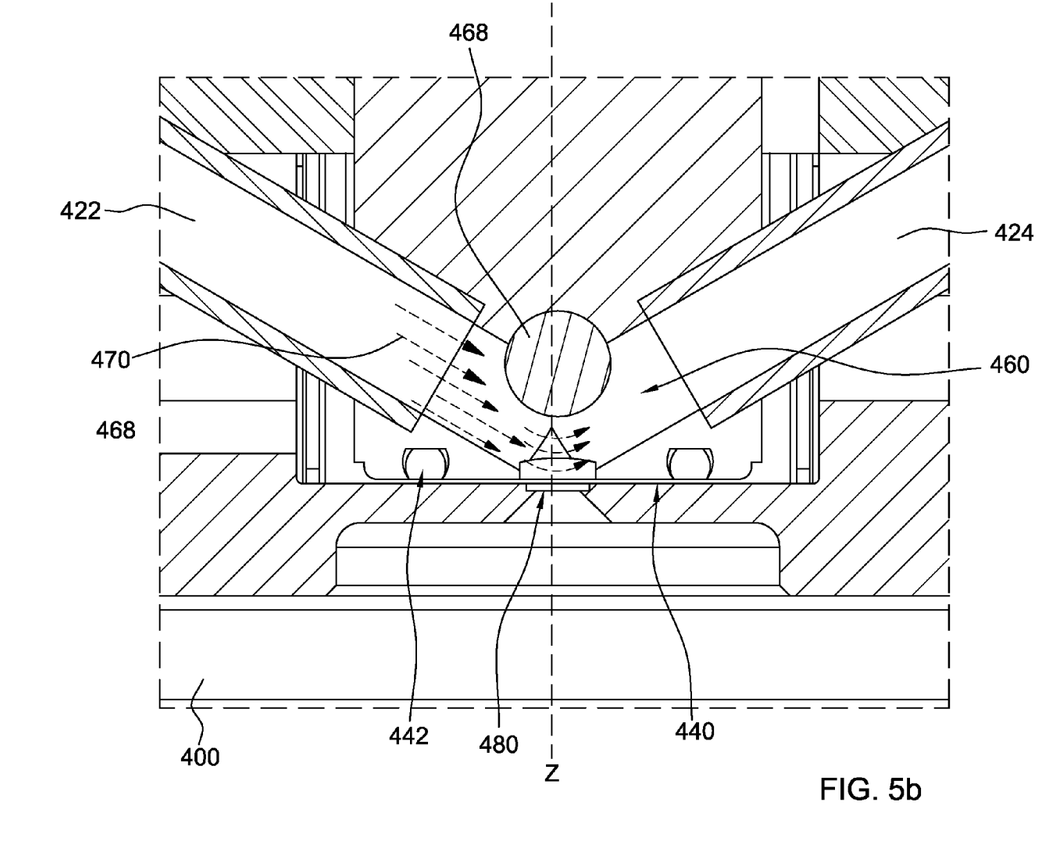

In accordance with the present invention, and with reference to the partial cross-sectional views of FIGS. 5*a-b*, an improved sample chamber 420 is provided. As above, the chamber includes input 422 and output 424 sample ports for, e.g., particulate, liquid or gas 470 moving through the system under pressure and requiring measurement in sample area 460. Moveable sample barrier 440 may separate the chamber 420 from the x-ray engine assembly 400 (portions of which are not shown but may be implemented in accordance with any of the above described techniques). Focal area 480 is defined by, e.g., the x-ray engine/optics discussed above for analyzing sample flowing through sample area 460. Sample area 460, formed in this example by the intersection of ports 422 and 424, is disposed over focal area 480. In accordance with the present invention, the otherwise unimpeded intersection of ports in sample area 460 is interrupted by a partial blocking structure 468.

With particular reference to the enlarged view of FIG. 5*b*, this blocking structure 468 significantly blocks sample flow in the upper section of sample area 468, while inducing increased sample flow rate directly proximate the focal area 480 and over barrier 440; or otherwise causing sample turbulence in this area. This increased sample flow rate and/or sample turbulence acts as a flushing mechanism to inhibit precipitate and/or other contamination of barrier 440 proximate focal area 480. Blocking structure may be implemented using any physical structure adequate to create the required turbulence, integrally formed in the chamber or otherwise affixed in the chamber. The structure shown in FIGS. 5*a-b* is a rounded (e.g., circular) pin, inserted into the otherwise uniform intersection area of ports 422 and 424; however, any suitable shape may be employed for the blocking structure. Also in the exemplary embodiment shown, structure 468 is disposed asymmetrically, slightly offset from central axis Z of the sample analysis area and/or x-ray focal area, slightly towards output port 424. This offset creates the necessary turbulence over focal area 480. Also shown in cross-section is o-ring 442, which facilitates a seal around in the sample chamber against barrier 440, in accordance with the above-incorporated U.S. Pat. No. 7,277,527.

Also in accordance with the present invention, and with reference to FIG. 5*a*, heating elements 490 can be applied prior to the sample analysis area in the form of, e.g., heat tape and/or heat blocks, and/or any other type of heating structure to modify the temperature of the incoming sample. Heating high viscosity sample streams is especially useful to thin the sample prior to the sample analysis area to enable smoother sample flows.

Figure 6:
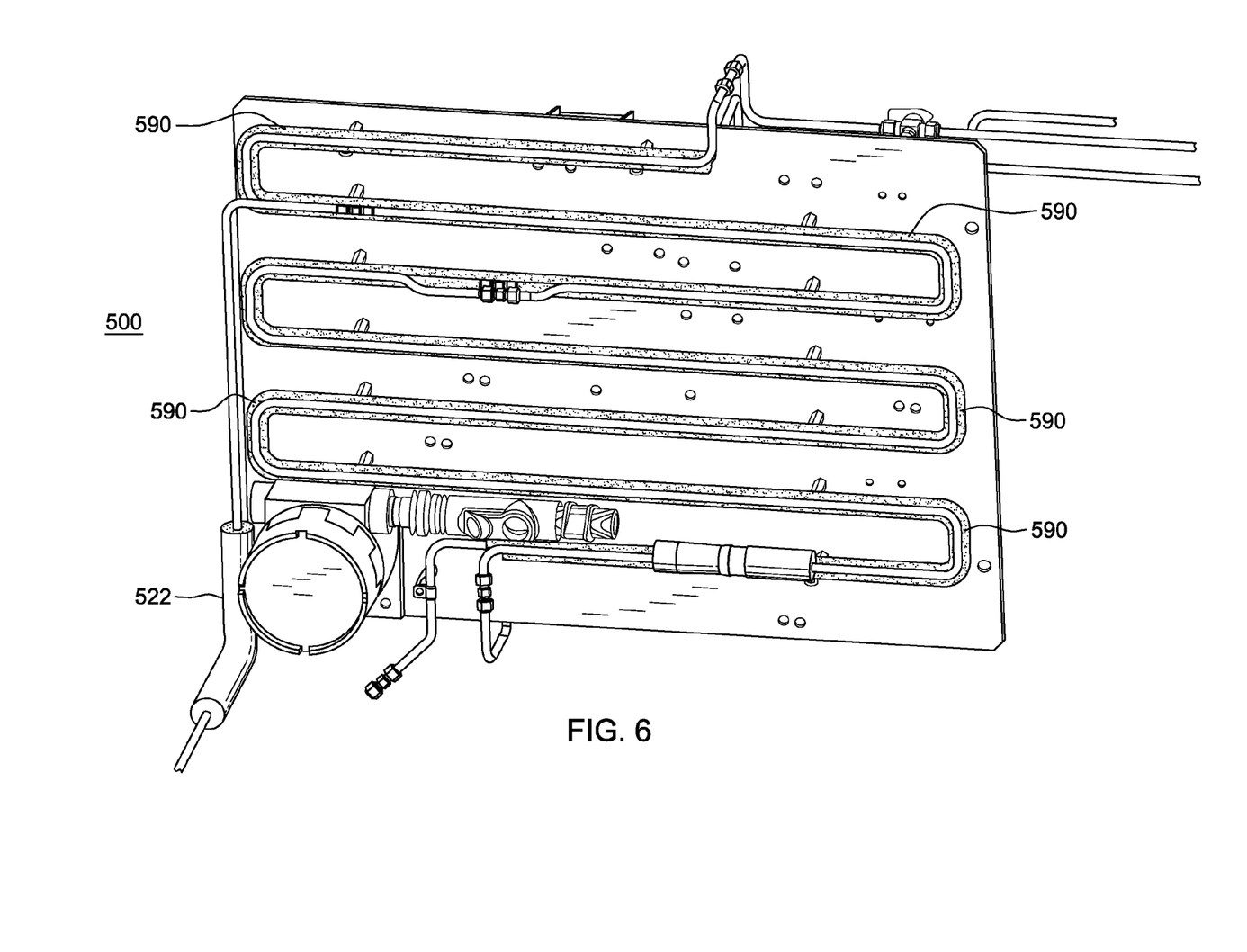
FIG. 6 is a manifold showing a potential application of heat tape to the input sample stream, in accordance with the principles of the present invention.

As shown in FIG. 6, a manifold 500 may support longer lengths of sample input tubes 522, along which longer lengths of heat tape 590 can be placed, prior to the sample stream's presentation to the sample chamber discussed above.

The present invention is especially useful in a real-time, on-line sample flow and analysis system for contaminant monitoring in crude oils and other heavy fuels, in refining applications. By measuring these contaminants real-time, fuel refineries will benefit from extended overall uptime, increased process efficiency, and improved safety. For such applications, the principles of the present invention may be used in combination with any of the disclosures of commonly-assigned U.S. Provisional Patent Application No. 61/498,889 filed on Jun. 20, 2011 and entitled ONLINE MONITORING OF CONTAMINANTS IN CRUDE AND HEAVY FUELS, AND REFINERY APPLICATIONS THEREOF, the entirety of which is hereby incorporated by reference.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An x-ray analysis sample handling apparatus, comprising:
   a sample chamber defining a sample analysis area within which a sample stream flows about an x-ray analysis focal area of an x-ray engine;
   an x-ray transparent barrier in a wall of said chamber for allowing x-rays to/from the sample analysis area;
   a blocking structure partially blocking the sample analysis area, for creating sample stream turbulence in the sample analysis area and over the barrier; and
   a heating element to heat the sample stream for improving flow of the sample stream.

2. The apparatus of claim 1, wherein the blocking structure is disposed asymmetrically about a central axis of the x-ray analysis focal area and/or the sample analysis area.

3. The apparatus of claims 2, wherein the blocking structure comprises a rounded pin.

4. The apparatus of claim 1 in combination with an x-ray analysis system, the x-ray analysis system comprising the x-ray engine including:
   an x-ray excitation path; and
   an x-ray detection path;
   wherein the x-ray excitation and/or the x-ray detection paths define the x-ray analysis focal area in said chamber.

5. The combination of claim 4, wherein the focal area is a focal point.

6. The combination of claim 5, wherein the focal point is defined by focused x-rays to/from at least one focusing optic in the x-ray excitation path and/or the x-ray detection path.

7. The combination of claim 6, wherein the at least one focusing optic is at least one curved diffracting optic or polycapillary optic.

8. The combination of claim 6, wherein the at least one focusing optic is at least one focusing monochromatic optic.

9. The combination of claim 8, wherein the at least one focusing monochromatic optic is a curved crystal optic or curved multi-layer optic.

10. The combination of claim 5, wherein at least one focusing optic in the x-ray detection path is positioned such that an input focal point thereof is at the x-ray focal point, and corresponds to an output focal point of at least one focusing optic in the x-ray excitation path.

11. The combination of claim 4, wherein the x-ray analysis system comprises a monochromatic wavelength-enabled XRF analyzer.

12. The combination of claim 11, wherein the analyzer is an MWDXRF or ME-EDXRF analyzer.

13. The apparatus of claim 1, wherein the sample comprises a petroleum-based product requiring the measurement of an analyte therein.

14. The apparatus of claim 1, wherein an analyte measured is at least one element chosen from the following list: S, Cl, P, K, Ca, V, Mn, Fe, Co, Ni, Cu, Zn, Hg, As, Pb, and Se.

15. The apparatus of claim 1, wherein the stream is crude oil, and an analyte measured is chlorine.

16. An x-ray analysis system comprising:

an x-ray engine having an x-ray source for producing an x-ray excitation beam, the x-ray excitation beam directed toward an x-ray analysis focal area;

a sample chamber for presenting a sample to the x-ray analysis focal area, the x-ray analysis focal area disposed within a sample analysis area defined within the chamber;

an x-ray detection path for collecting secondary x-rays from the focal area and directing the secondary x-rays toward a detector;

an x-ray transparent barrier on a wall of the chamber through which the x-ray excitation beam and the secondary x-rays pass;

a blocking structure partially blocking the sample analysis area, for creating sample stream turbulence in the sample analysis area and over the barrier; and a heating element to heat the sample stream for improving flow of the sample stream.

17. The system of claim 16, wherein the analyzer comprises a monochromatic wavelength-enabled XRF analyzer.

18. The system of claim 17, wherein the system is an MWDXRF or ME-EDXRF analyzer.

19. The system of claim 16, wherein an analyte measured is at least one element chosen from the following list: S, Cl, P, K, Ca, V, Mn, Fe, Co, Ni, Cu, Zn, Hg, As, Pb, and Se.

20. The system of claim 16, wherein the stream is crude, and an analyte measured is chlorine.

* * * * *